United States Patent [19]
Schneider

[11] Patent Number: 5,330,422
[45] Date of Patent: Jul. 19, 1994

[54] DEVICE FOR REMOVING A BIOPSY FLUID SAMPLE FROM A BODY CAVITY

[75] Inventor: Aaron Schneider, St. Petersburg, Fla.

[73] Assignee: Biological Tissue Reserve, Inc., St. Petersburg, Fla.

[21] Appl. No.: 149,622

[22] Filed: Nov. 9, 1993

[51] Int. Cl.⁵ .................................................. A61M 1/00
[52] U.S. Cl. ...................................... 604/27; 128/766; 604/170
[58] Field of Search ................ 604/170, 200, 206, 27, 604/248; 128/763, 766, 767, 768, 769

[56] References Cited

U.S. PATENT DOCUMENTS

| | | | |
|---|---|---|---|
| 3,864,213 | 2/1975 | Bucalo | 128/769 |
| 4,036,232 | 7/1977 | Genese | 128/766 |
| 4,405,308 | 9/1983 | Jessup | 604/200 |
| 4,808,158 | 2/1989 | Kreuzer et al. | 604/170 |
| 4,895,168 | 1/1990 | Machek | 604/170 |
| 4,923,441 | 5/1990 | Ruler | 606/170 |
| 5,083,572 | 1/1992 | Pokorny | 604/27 |
| 5,181,909 | 1/1993 | McFarlane | 604/200 |

Primary Examiner—Paul J. Hirsch
Attorney, Agent, or Firm—Walter J. Monacelli

[57] ABSTRACT

The device shown herein is made of essentially two parts one of which parts is essentially a hollow tube closed for a substantial distance at one end having a hollow cap with only a side opening therein. The second part is a rod with an end portion adapted to snugly fit into the interior of the cap of the first part. This second part is rotatable on its linear axis and when held in a particular axial position, the second part end portion is adapted to block the side opening so as to cut off communication between the interior and the exterior of this cap. This second part end portion has a cut-away section so that when this second part is rotated axially, preferably in the neighborhood of 180°, this cut-away section is positioned adjacent to the side opening of the cap of the first part thereby allowing communication of fluid through the opening in said cap.

3 Claims, 2 Drawing Sheets

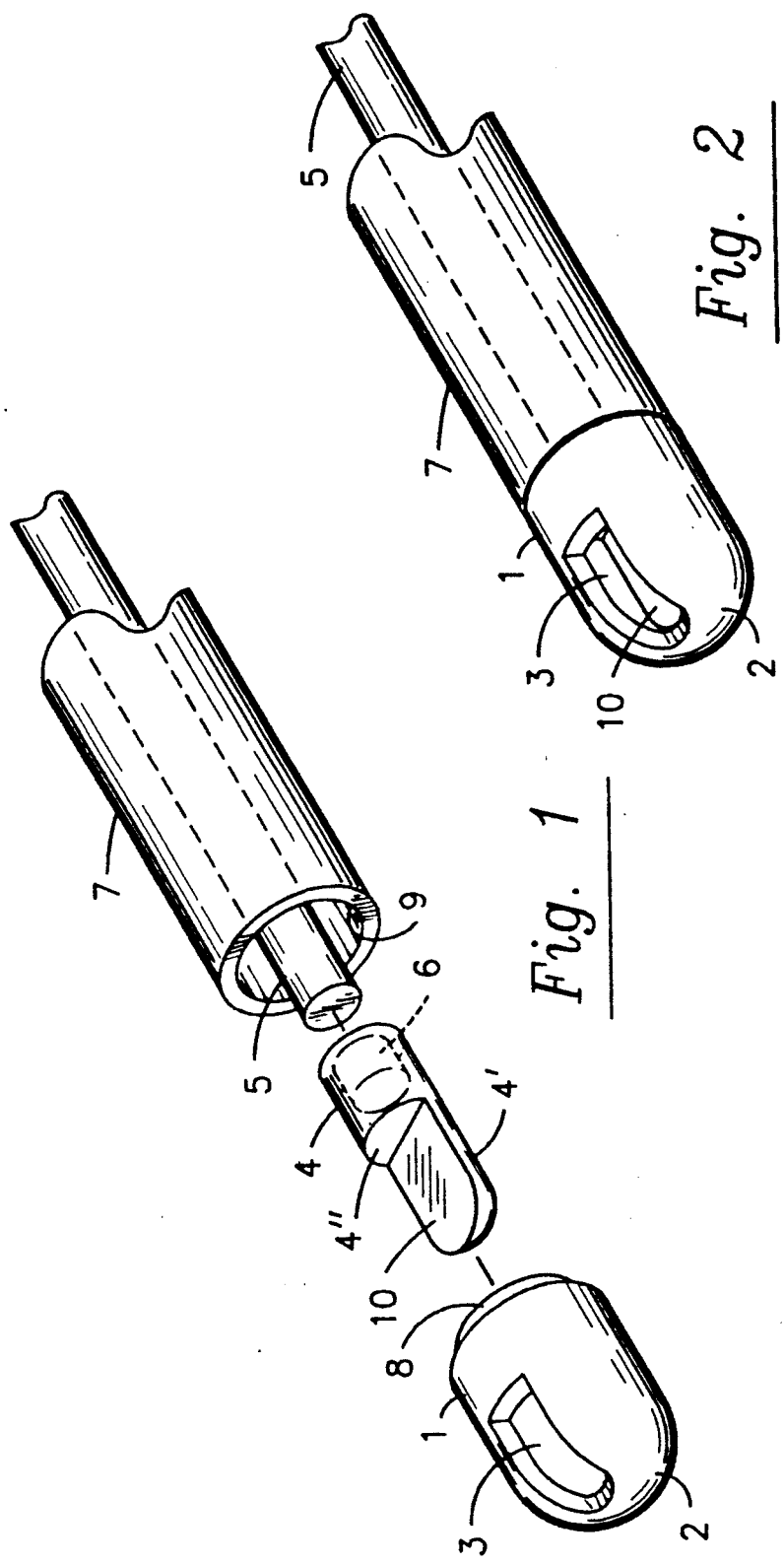

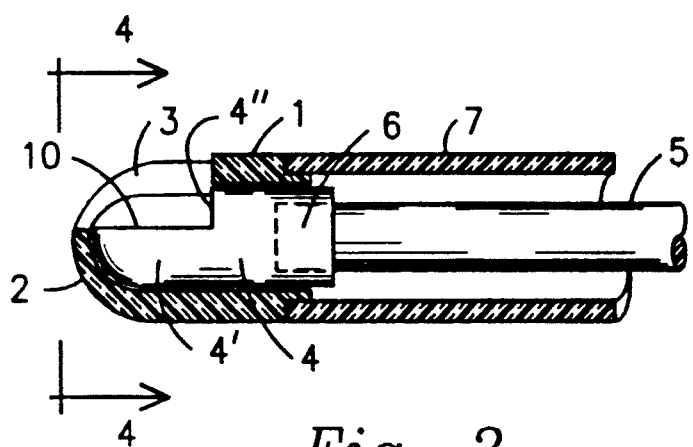
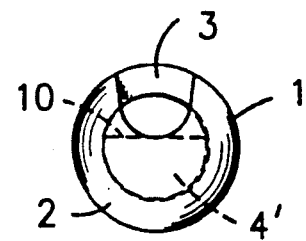
Fig. 3    Fig. 4
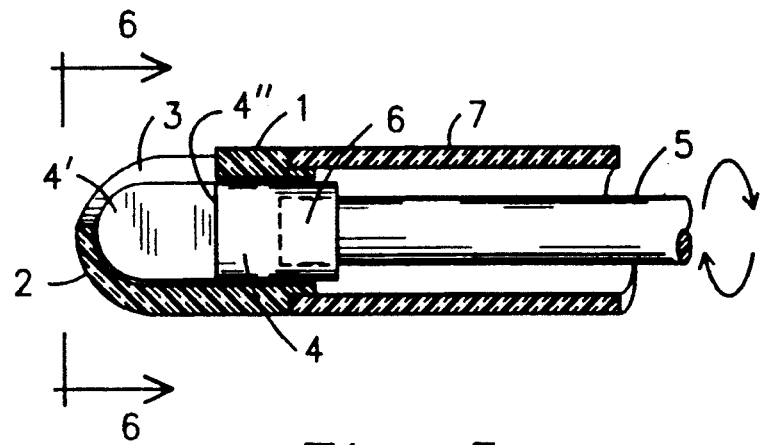
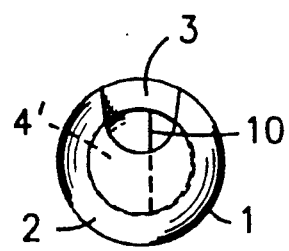
Fig. 5    Fig. 6
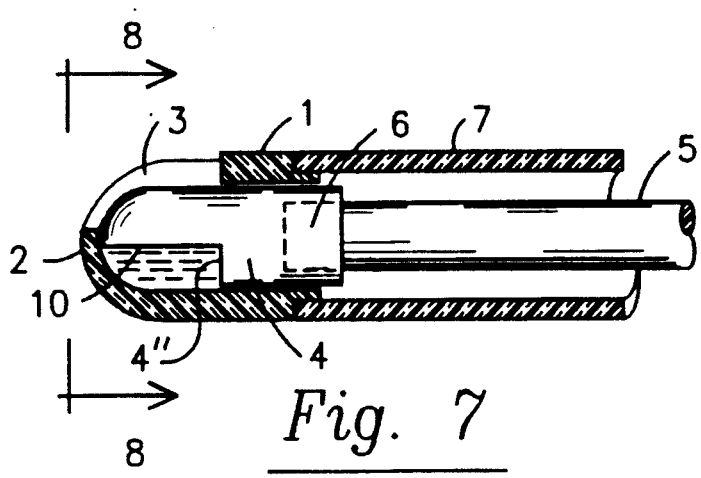
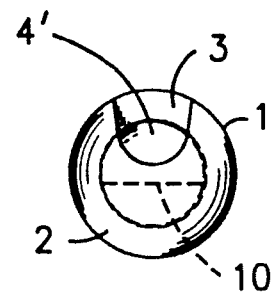
Fig. 7    Fig. 8

DEVICE FOR REMOVING A BIOPSY FLUID SAMPLE FROM A BODY CAVITY

BACKGROUND OF THE INVENTION

1. Field of the Invention

This invention relates to a device for removing fluid biopsy samples from a body cavity. More specifically, it relates to a two-part device, a second part substantially inside a first part. Still more specifically, it relates to an interior cavity in an end portion of the first part adapted to receive a fluid biopsy sample through a side opening in said cavity. Still more specifically, the second part is adapted to rotate on its linear axis and by such linear rotation to control the position of a portion of the second part which permits the flow or non-flow of fluid biopsy sample into or out of the cavity in said first part.

2. State of the Prior Art

In the determination of biopsy tests on fluids within parts of the body it is desirable to remove and recover samples of the fluid. Rather crude methods have been made to retrieve samples of these fluids for biopsy tests.

In one such present method a device which has a top or cap for a test tube with two sticks projected downward from the cap and into the tube which is a sterile culture sensitive test tube. The two sticks are each wrapped at the lower end thereof with a cotton swab. The top or cap is removed from the tube carrying with it the swab wrapped sticks. These cotton swabs are dipped into the body fluid for which biopsy tests are to be performed so as to absorb samples of the same into the cotton. Then sticks are reintroduced into the tube and the cap top recapped onto the open end of the test tube. This method permits the fluid samples to be unprotected against contact with air bacteria and contaminated with the same.

OBJECTIVES

It is an object of this invention to provide a simple device to obtain samples of fluid from a body cavity for biopsy tests.

It is also an object of this invention to provide a device which is capable of recovering fluid biopsy test samples from open or "closed" body cavities.

It is also an object of this invention to obtain such fluid samples under controlled conditions which eliminate or substantially reduce the possibility of exposing the fluid sample to contaminating conditions.

It is also an object of this invention to provide a fluid sample recovering device which can be easily controlled and manipulated to give a substantial amount of the desired fluid.

It is also an object of this invention to provide a device which can be easily and effectively sterilized for repeated reuse of the same.

Other objects will become obvious upon reading the details of this invention as described below.

BRIEF DESCRIPTION OF THE DRAWINGS

FIG. 1 is an exploded perspective view of a preferred modification of the device of this invention.

FIG. 2 is a perspective assembled view of the parts shown in FIG. 1.

FIG. 3 is a longitudinal cross-sectional view taken of the assembled device of FIG. 2.

FIG. 4 is an end view of the device shown in FIG. 3.

FIG. 5 is a view similar to that of FIG. 3 except that there has been a partial rotation of the interior portion on its linear axis.

FIG. 6 is an end view of the device shown in FIG. 5.

FIG. 7 is a longitudinal cross-sectional view similar to that of FIG. 5 except that communication between the interior and exterior of the opening in the device has been completely blocked and liquid is retained in this cavity.

FIG. 8 is an end view of the device shown in FIG. 7.

DESCRIPTION OF THE PREFERRED EMBODIMENTS

In the exploded view of FIG. 1, cap 1 has essentially a cylindrical outer shape and has a first end 2 as a closed end essentially curved, preferably with the terminal portion in the shape of a hemisphere. This curved first end has an opening 3 which advantageously extends to the side of the cap and allows communication or fluid flow from the outside to the inside of the cap or vice versa. The cap is hollow and has a shape and size of interior to allow for the entrance and snug fit of plug 4 to the interior of cap 1 by attachment to the second end of cap 1. Plug 4 has an essentially cylindrical outer surface to allow for axial rotation inside the cap. In FIG. 1 the underside 4' of the plug retains the cylindrical configuration but the upper portion is cut away to provide a surface which is preferably flat but may have other shapes so long as it provides an open space between the plug portion 4' and the interior cavity of cap 1.

Rod 5 is axially aligned with plug 4 and is affixed as shown in FIG. 2. This fixture may be effected by having a cylindrical opening 6 into which rod 5 is snugly introduced or the rod 5 and plug 4 may be one integrated unit. The rotation of rod 5 on its linear axis simultaneously rotates plug 4 so that the cut-away section adjacent to surface 4" can be adjusted to various positions within the interior cavity of cap 1. With such rotational adjustments the curved or cylindrical surface 4' can be positioned adjacent to opening 3 so as to cut off fluid flow through opening 3. Other rotational axial adjustments can position the cut-away section adjacent to surface 4" so that fluid flow can be effected through opening 3 either into or out of the cavity portion of cap 1. Sleeve 7 has a cylindrical shape preferably conforming essentially in size or outer diameter with the cylindrical portion of cap 1. Cap 1 has a lip 8 protruding from the inside edge of cap 1. This edge is designed in shape and size to fit snugly into the interior cylindrical surface 9 of sleeve 7 so that sleeve 7 can be rigidly attached to cap 1. The diameter of the inside sleeve surface 9 is also large enough to allow passage of plug 4 through the interior of sleeve 7 thereby allowing for the insertion of plug 4 into the interior of cap 1 and provide a snug fit between the interior surface of cap 1 and the exterior cylindrical surface of plug 4 thereby preventing excessive leakage or passage of fluid between those two surfaces. The free passage of plug 4 through the interior of sleeve 7 also accommodates the removal of plug 4 for cleaning and sterilizing.

When a fluid sample is trapped or contained in the cavity in cap 1, the cap is held in a position with the opening 3 at a vertically upward position for transmittal to the desired receptacle and fluid poured into the desired receptacle by rotating cap 1 on its linear axis, with opening 3 unblocked by surface 4" so that the fluid may be transferred as desired.

FIGS. 3 and 4 show plug 4 rotated to a position where cut-away section 4" has surface 10 facing upward so that there is free fluid communication between cut-away section 4" and opening 3. In this position fluid can be admitted to or emptied from the cavity of cap 1.

FIGS. 5 and 6 show the device rotated about 90° from the position in FIGS. 3 and 4 so that there is only partial blocking of the passageway between opening 3 and the cavity in cap 1.

FIGS. 7 and 8 show plug 4 rotated 180° from the position of FIGS. 3 and 4 so that the captured fluid is retained between the surface 10 of plug sections 4 and 4'. Fluid communication with opening 3 is cut off by plug section 4'.

When it is desired to collect fluid, the cap of the device is inserted in the body cavity with the 4' part of plug 4 in the position shown in FIGS. 3 and 4 wherein opening 3 is completely unblocked, or even in the position shown in FIGS. 5 and 6 where there is only partial blockage of opening 3. When fluid has flown into the cavity of cap 1 unoccupied by plug 4 (and 4'), the plug is axially rotated to move plug 4' into position to block opening 3 and thereby prevent escape of the captured fluid while it is being transported and transferred to a desired receptacle.

Other modifications in the use of the improved device of this invention will become obvious upon use of the device.

The device of this invention is preferably made of plastics, the particular type being selected according to the particular fluids with which the device will be used and also dependent on the various molding and fabricating problems presented. Other appropriate materials such as metals may be used.

While certain features of this invention have been described in detail with respect to various embodiments thereof, it will of course be apparent that other modifications can be made within the spirit and scope of this invention, and it is not intended to limit the invention to the exact details insofar as they are defined in the following claims.

The invention claimed is:

1. A device for removing fluid from a human body cavity for the determination of a biopsy test thereon comprising:
   (a) a hollow cap having a cylindrically shaped outer surface and having a first end and a second end, said cap being closed at said first end except for an opening extending from the interior to the exterior of said cap, and said cap having a hollow cylindrical shape at said second end;
   (b) a rod of substantial length having attached at one end thereof a plug having its outer configuration and size appropriate to fit snugly against the interior surface of the closed end of said cap, except that said plug has a cut-away section which is capable of being positioned at said opening and is also capable of being rotated to a position away from said opening, and when positioned at said opening in said cap, will allow free fluid flow between said cut-away section and the exterior of said cap;
   (c) a sleeve of substantial length but shorter than the length of said rod, said sleeve having an inside diameter greater than the outer diameter of said plug and adapted to allow free passage of said plug along the length of said sleeve, said sleeve being attached at one end thereof to the said open end of said cap and in axial alignment therewith; whereby the device will admit the flow of fluid into the interior of said cap when the cut-away section of said plug is positioned at said cap opening and when the plug is rotated on its linear axis and whereby fluid communication between said opening and said cavity is cut off by rotating the plug to position the cut-away section away from said cap opening so that the fluid will be retained within the cavity.

2. The device of claim 1 in which the closed end of said cap has the shape of a hemisphere except for the opening in said cap.

3. The device of claim 2 in which said cap opening extends from near the top of said hemisphere to the cylindrical shape of said cap.

* * * * *